US011633613B1

(12) United States Patent
Shaker et al.

(10) Patent No.: US 11,633,613 B1
(45) Date of Patent: Apr. 25, 2023

(54) COMPACT AED WITH EXTERNAL ELECTROCARDIOGRAM

(71) Applicant: ALTRIX MEDICAL, INC., Centreville, VA (US)

(72) Inventors: Matthew Robert Shaker, Centreville, VA (US); Daniel Fleck, Potomac, MD (US); Jesse S. Kruska, Westport, CT (US)

(73) Assignee: Altrix Medical, Inc., Centreville, VA (US)

( * ) Notice: Subject to any disclaimer, the term of this patent is extended or adjusted under 35 U.S.C. 154(b) by 0 days.

(21) Appl. No.: 17/969,370

(22) Filed: Oct. 19, 2022

Related U.S. Application Data

(63) Continuation-in-part of application No. 17/878,992, filed on Aug. 2, 2022, which is a continuation of application No. 17/712,881, filed on Apr. 4, 2022, now Pat. No. 11,433,249.

(51) Int. Cl.
*A61N 1/39* (2006.01)
*A61N 1/04* (2006.01)

(52) U.S. Cl.
CPC .......... *A61N 1/3904* (2017.08); *A61N 1/046* (2013.01); *A61N 1/0492* (2013.01)

(58) Field of Classification Search
None
See application file for complete search history.

(56) References Cited

U.S. PATENT DOCUMENTS

| | | | |
|---|---|---|---|
| 8,798,743 B1 * | 8/2014 | Khuon | A61B 5/053 607/5 |
| 10,799,709 B2 * | 10/2020 | Teber | A61N 1/3925 |
| 11,197,631 B2 | 12/2021 | Liu et al. | |
| 2002/0156506 A1 * | 10/2002 | Kroll | A61N 1/3904 607/5 |
| 2013/0282072 A1 | 10/2013 | Abdeen et al. | |
| 2014/0100497 A1 | 4/2014 | Hayashi et al. | |
| 2014/0107541 A1 | 4/2014 | Sullivan et al. | |
| 2014/0277225 A1 | 9/2014 | Quan et al. | |
| 2014/0277228 A1 | 9/2014 | Quan et al. | |
| 2014/0317914 A1 * | 10/2014 | Shaker | A61N 1/046 29/825 |
| 2015/0273226 A1 * | 10/2015 | Einy | A61N 1/3968 607/6 |
| 2017/0056682 A1 * | 3/2017 | Kumar | G16H 50/20 |
| 2017/0361120 A1 | 12/2017 | Liu et al. | |
| 2020/0282225 A1 * | 9/2020 | Kumar | A61N 1/046 |

* cited by examiner

*Primary Examiner* — Eric D. Bertram
(74) *Attorney, Agent, or Firm* — Louis Ventre, Jr.

(57) ABSTRACT

A compact automated external defibrillator (AED) is a device configured to receive electrocardiogram signals while the AED's electrode pads are in airtight storage. A surface of the device has a first electrical connection and a second electrical connection to a circuit board, each at a separate defined location on the surface. The circuit board receives ECG signals from a patient when the first defined location and the second defined location on the surface of the device body are put in contact with the patient. The circuit board may be configured to sense ECG signals from the patient through a plurality of additional defined locations on the surface of the device.

13 Claims, 13 Drawing Sheets

COMPACT AED WITH EXTERNAL ELECTROCARDIOGRAM

CROSS-REFERENCE TO RELATED APPLICATIONS

This application is a continuation-in-part of prior U.S. application Ser. No. 17/878,992, filed 2 Aug. 2022, which is a continuation of U.S. application Ser. No. 17/712,881, filed 4 Apr. 2022, now U.S. patent Ser. No. 11/433,249, issued 6 Sep. 2022, which are hereby incorporated by reference herein in their entireties.

TECHNICAL FIELD

In the field of light, thermal, and electrical application, a device for applying electrical energy to the external surface and inside portions of the body to restore normal operation of the heart.

BACKGROUND ART

The International Electrotechnical Commission (IEC) is a worldwide organization for standardization comprising all national electrotechnical committees (IEC National Committees). The object of IEC is to promote international co-operation on questions concerning standardization in the electrical and electronic fields. The IEC publishes a standard for Medical electrical equipment at Part 2-4: Particular requirements for the basic safety and essential performance of cardiac defibrillators IEC 60601-2-4, which discusses requirements for the basic safety and essential performance of cardiac defibrillators. Among other things, it specifies requirements for the automated external defibrillator (AED) electrodes. This governing standard is used to develop and package pads for defibrillators.

This disclosure leverages the relatively small and compact nature of the device body of the AED described in parent U.S. Pat. No. 11,433,249 and parent pending application Ser. No. 17/878,992. An innovative concept in the present disclosure builds on the nature of the compact AED by utilizing integrated surface electrodes operationally connected to the circuit board and physically located directly on a surface of the device body, to wit, the relatively small case storing the compact AED.

To easily take an ECG on any patient at any time, the device body with these surface electrodes may be simply placed on a patient. Alternatively, if convenient to the circumstances, the patient may simply touch the surface electrodes, which would then permit the compact AED to take an ECG. This physical feature enables taking an ECG without unpacking and without attaching the AED pads, using hydrogel, or needing any disposable supplies.

The parent application and the parent patent utilize AED electrodes that are compliant with the IEC standard (with the possible exception of cord length, which may be less than the standard but such new length is justified by the fact that the improvements discussed herein enable the automated external defibrillator pads (AED pads) to be in closer proximity to the device body when used as compared to other AEDs.

An AED typically uses two electrodes, each with a conductive gel to help transfer an AED shock to a patient. The standard calls for the minimum active gel area of self-adhesive electrodes to measure a total of 150 square centimeters, with each area being at least 50 square centimeters for adults. Pediatric pads are required to total 45 square centimeters, with each area being at least 15 square centimeters (when pediatric electrodes are used).

Most AEDs today have electrode pads that are the same size and package these electrode pads either in the AED or a larger AED carrying case. The electrodes with pads are typically sealed in a pouch, but there are other packaging methods. When the AED is used, the pouch is removed from the AED and then the AED pads are removed from the pouch prior to attaching to a patient. A protective layer is typically peeled from the electrode pad, revealing an adhesive layer for attachment to the patient. The adhesive is conductive and typically a hydrogel formula. The electrodes with electrode pads are adhered to the patient in specified locations.

SUMMARY OF INVENTION

The "Compact AED with External Electrocardiogram" is configured to receive ECG signals (electrocardiogram signals) from a patient while an AED proximate pad and an AED distal pad are stored in a way that limits exposure to air that could dry out the AED pads.

Operable components in the device body include the proximate pad; an AED proximate electrode, the AED distal pad; an AED distal electrode; and a circuit board.

A surface of the device body has a first electrical connection to the circuit board. The first electrical connection is at a first defined location on a surface of the device body. The first electrical connection may be the AED proximate electrode. The surface is configured to avoid increasing air exposure of the AED pads.

A second electrode at a second defined location on the surface of the device body provides a second electrical connection to the circuit board. The circuit board is an indivisible unit configured to receive the ECG signals from a patient when the first defined location and the second defined location on the surface of the device body are put in contact with the patient.

The proximate electrode may coincide with the first defined location and the AED distal electrode attached to the AED distal pad may be electrically connected to the second defined location. An on-off switch may be installed between the second electrical connection and the distal electrode. The on-off switch is configured to prevent electrical flow between the AED distal electrode and the circuit board when the on-off switch is set to off.

The AED distal electrode and the AED proximate electrode are configured to deliver an electrical charge when the AED proximate pad and the AED distal pad are attached to the patient. The electrical charge is controlled by no other circuit board positioned outside the device body, i.e., the storage case.

The circuit board may be configured to sense ECG signals from the patient through a plurality of additional defined locations on the surface of the device body. Also, the additional defined locations are further configured to sense the ECG signals when the additional defined locations are in electrical contact with the patient.

The circuit board may receive ECG signals from a plurality of ECG sensors beyond the two in a basic implementation. This plurality of ECG signals may include signals from more than two ECG sensors configured to connect to the first defined location and/or to the second defined location.

Each of the defined locations may be connected to a plurality of ECG sensors. The AED may further include a speaker configured to audibly indicate the ECG signals. The AED may include a screen configured to display the ECG signals.

The device body may be connected wirelessly to a computer for display and for audible indications of the ECG signals.

Technical Problem

An ElectroCardio Gram (ECG), or sometimes referred to as an EKG, is used by AEDs to diagnose shockable arrhythmias. An ECG is also a common medical procedure performed to evaluate and baseline patient conditions. Taking an ECG is usually done by placing wired sensors on a patient. In AEDs, AED pads with integrated sensors are attached to the patient. ECG signals are sensed through the AED pads. Deploying AED electrode pads is not optimal for ECG acquisition as their placement and number (i.e., two) provide an inferior view of the heart when compared to other types of ECGs. Moreover, AED pads are typically single use items that require replacement after their use. For that reason, ECGs administered using an AED are intended for the emergency assessment of shockable arrythmias and are not for other patient assessments. Moreover, even though AEDs have fundamental circuitry required to take an ECG, their size does not provide significant advantages over either at-home or advanced ECG machines.

An ECG can be taken using wires attached to the patient, which is typically performed employing larger devices, including weighty, bulky AED devices. Having to use larger, heavier, bulkier and wired equipment impedes prompt patient treatment and may lengthen the AED and the ECG processes.

Solution to Problem

The solution to the problem is providing a compact AED with the capability to take an ECG without unpacking the AED proximate pad and the AED distal pad.

The solution to the problem is locating ECG electrodes on a surface of the compact AED storage package, to wit, the device body, that can simply be put in contact with the patient without changing the airtight status involving the AED proximate pad and the AED distal pad.

The solution to the problem is an improvement to the previously patented compact automated external defibrillator (AED) (U.S. Pat. No. 11,433,249 and pending application Ser. No. 17/878,992) providing an ECG capability without attaching AED pads to a patient.

The solution to the problem is a unique and improved way to take an electrocardiogram (ECG) while the AED pads are in a relatively airtight, and undeployed position within the compact AED.

The solution to the problem is providing a complete electrical circuit through a compact AED circuit board using electrodes fixed and accessible on an external surface of the device body.

The solution to the problem is to provide access to the AED circuit board for ECG purposes without having to utilize the AED proximate pad or the AED distal pad.

The solution to the problem is to enable a compact AED to take an ECG of a patient without exposing the proximate pad or the AED distal pad to the air.

The solution provides a minimum of two electrodes on a surface of the AED storage package, to wit, the device body. These electrodes are available to take an ECG while the disposable AED pads remain stored and protected against exposure to the drying effects of the air.

In one embodiment, the solution provides the ability to remove a portion of the AED device body containing the sealed AED pads, thereby exposing a minimum of two electrodes on a surface of the AED device body.

Advantageous Effects of Invention

The improvement described herein recognizes that taking an ECG is a common medical procedure desired for use to evaluate and baseline many patient conditions. Thus, this improvement enables an easier, more accurate, and more mobile method for assessment of emergency and non-emergency medical conditions. It enables an emergency medical technician (EMT) to take the ECG using a compact AED by deploying the AED pads. The EMT no longer has to utilize a large, heavier AED or ECG device.

This improvement also allows non-medically trained people to easily and quickly take their own ECGs outside of medical environment without deploying the AED pads, allowing an emergency medical device to also become a health care maintenance application that can be used to record, track and report important diagnostic data (e.g., to a medical provider).

When cartridges are used to hold components of the AED, the improvement allows a disposable cartridge (1120) that contains the sealed pads to be removed and replaced with a second disposable cartridge containing 10 electrodes with hydrogel. These 10 electrodes are configured to be electrically connected through terminals on a surface (1115) of the device body (105). Such an alternate disposable AED device body can be used by medical personal to obtain a traditional 12-lead ECG, providing a mobile ECG platform that doubles as an AED by simply replacing the disposable cartridge (1120).

The solution disclosed herein employs an alternative configuration for the AED where the AED attaches to the patient, requiring only one remote pad for operability.

The preferred solution disclosed herein strives to minimize duplication of component parts within the AED to provide an AED operable with fewer component parts than AEDs heretofore available.

The solution disclosed herein provides a reusable AED once the AED pads are replaced, which reduces replacement costs and adds to functionality.

The solution disclosed herein extends the life of the AED by allowing hydrogel, or other adhesive, to be replaced prior to or after expiration.

The solution enables the use of pads having different sizes, and complies with IEC60601-2-4 requirements for total area and minimum individual area.

The solution also allows for re-use of AED electrodes and circuitry to provide for on-demand single lead ECG, on-demand 6-lead ECG, and 12-lead ECG for purposes over and above determination of shockable arrhythmias or cardiopulmonary resuscitation (CPR).

BRIEF DESCRIPTION OF DRAWINGS

The drawings illustrate preferred embodiments of the Compact AED with External Electrocardiogram according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

In the following description, reference is made to the accompanying drawings, which form a part hereof and which illustrate several embodiments as disclosed herein. The drawings and the preferred embodiments of the Compact AED with External Electrocardiogram are presented with the understanding that the Compact AED with External Electrocardiogram is susceptible of embodiments in many different forms and, therefore, other embodiments may be utilized and structural, and operational changes may be made, without departing from the scope of the present invention.

Figure 1:
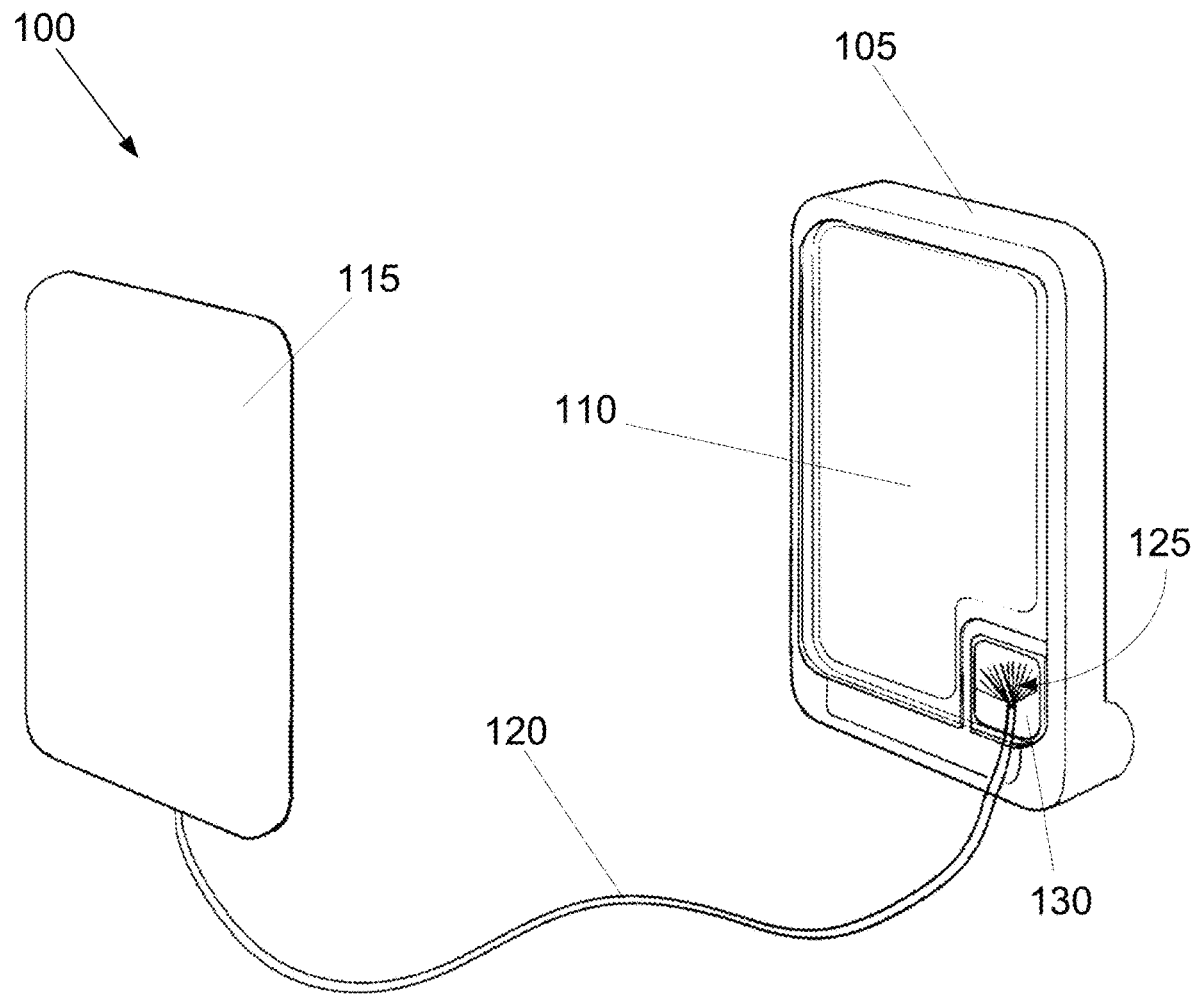
FIG. 1 is a perspective of the distal electrode separated from the device body.
Figure 4:
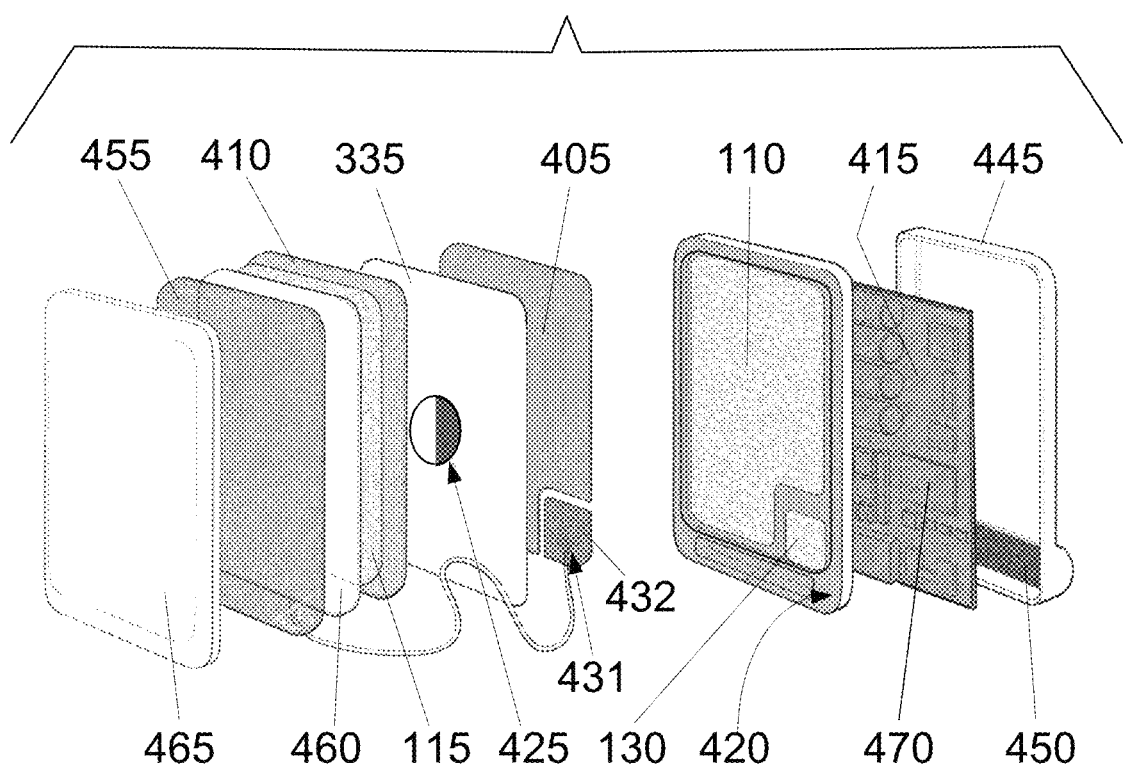
FIG. 4 is an exploded view of the compact AED with one distal electrode.
Figure 5:
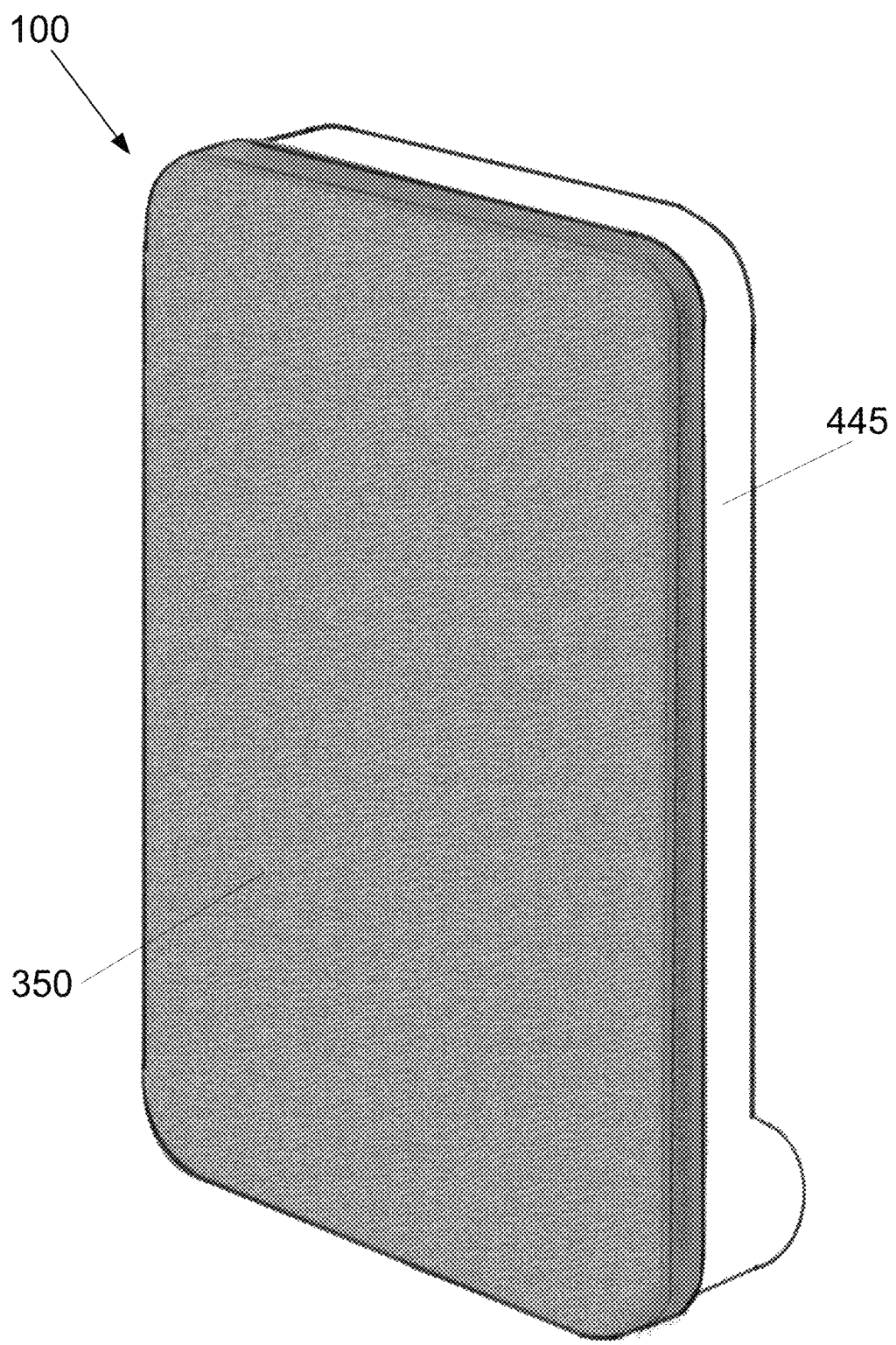
FIG. 5 is a perspective view of the rear of the compact AED with one distal electrode.
Figure 6:
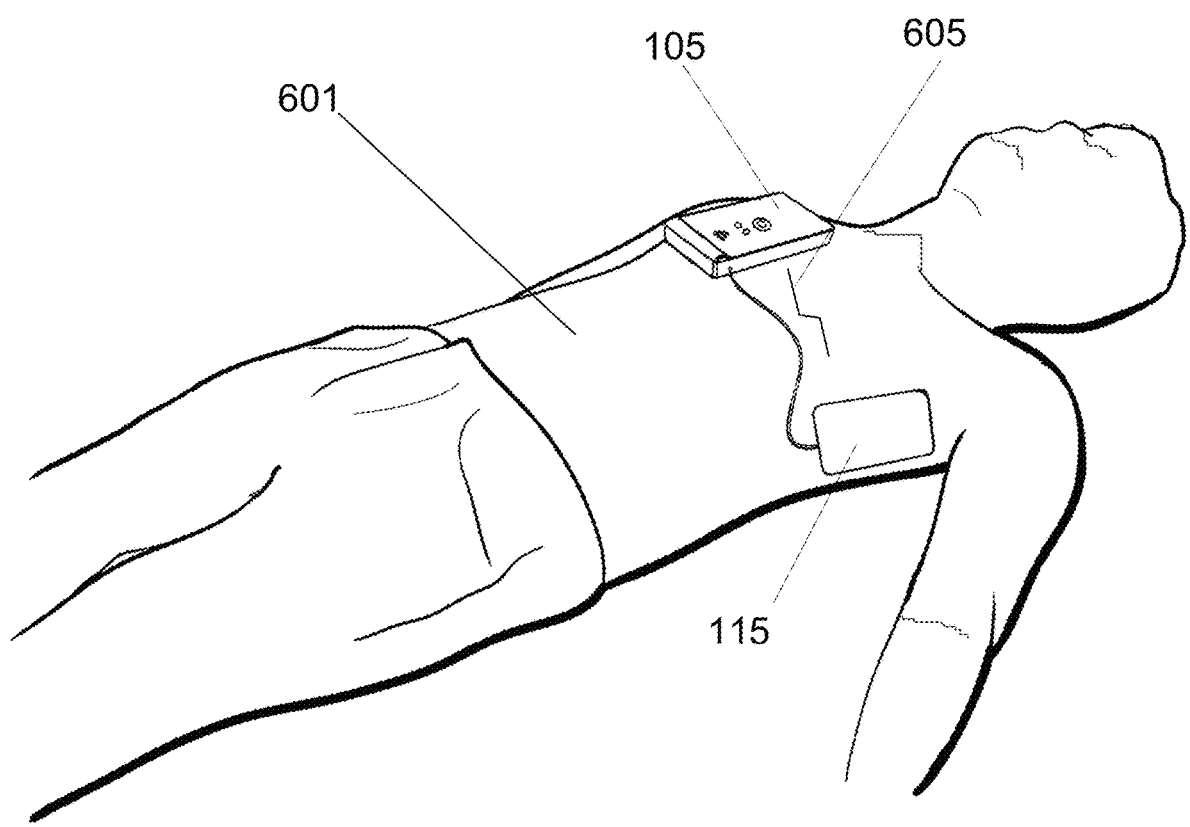
FIG. 6 is a perspective view of a patient in cardiac distress with the compact AED with one distal electrode attached to the patient.

FIG. 1 is a front perspective view of an embodiment of the compact AED (100) with external electrocardiogram. It includes an AED distal electrode (115) shown separated from its storage position in the device body (105). The compact AED (100) may be referred to herein as the AED. FIG. 4 shows an exploded view of important components of the compact AED (100).

Figure 11:
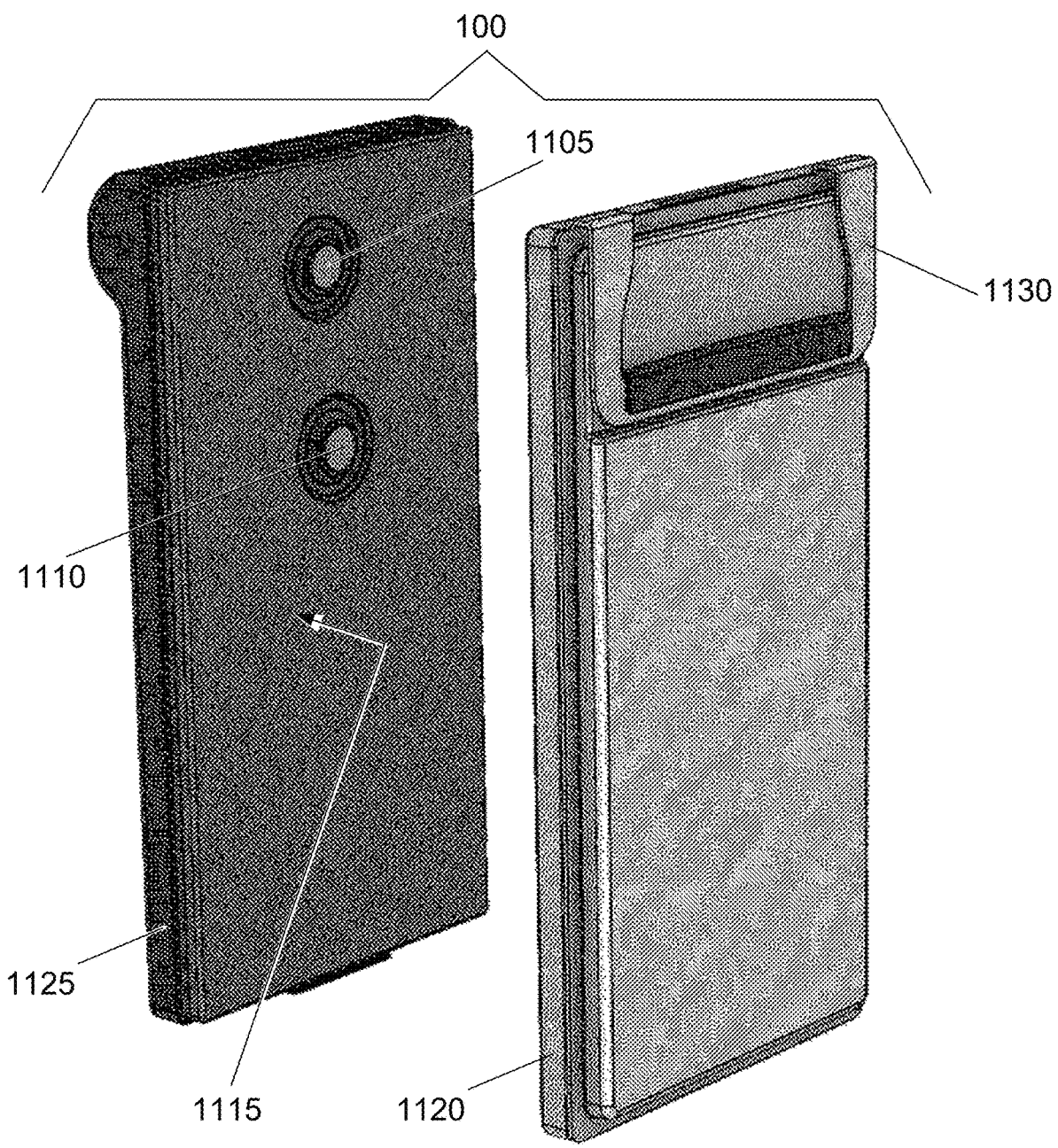
FIG. 11 is a rear perspective exploded view of the device body separated into at least one airtight cartridge and showing ECG electrodes on an internal surface that is exposed upon separating the cartridges.
Figure 12:
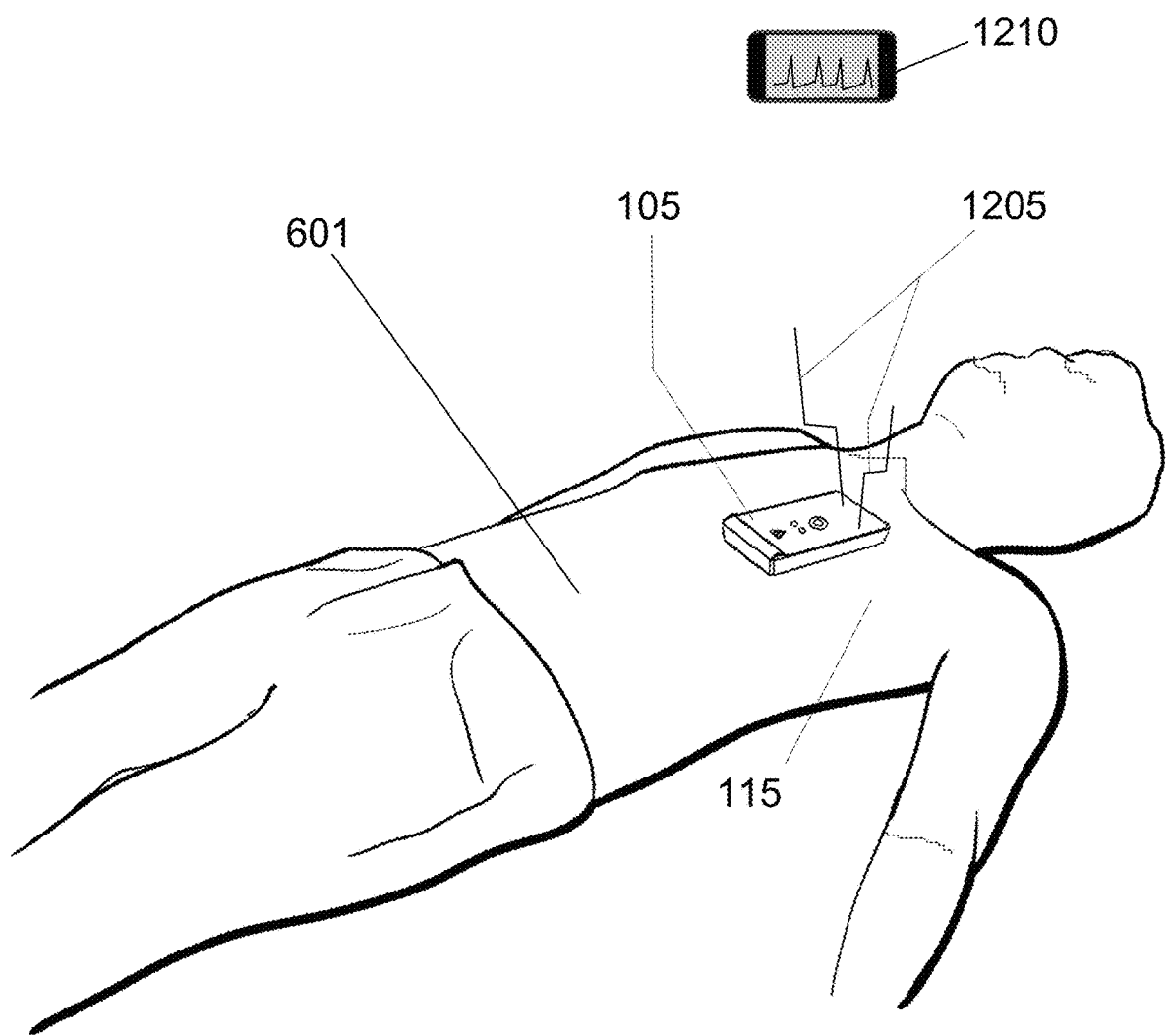
FIG. 12 is a perspective view of a patient showing an example placement of the device body to take and ECG.

FIG. 11 shows an exploded view of a preferred embodiment of the compact AED (100) with external electrocardiogram having at least one air-tight component, or cartridge, where the AED pads are stored. The compact AED (100) is initially packaged within a device body (105) configured to compactly store the AED components. FIG. 11 shows the device body (105) separated into two cartridges that are joined together to make the compact AED (100).

The first of these two cartridges on the left in FIG. 11, is a circuit-board cartridge (1125) that houses the circuit board (415). The circuit-aboard cartridge may be thought of as permanent and reusable.

The second of these two cartridges on the right in FIG. 11, is a disposable cartridge (1120) that houses the AED pads. The disposable cartridge (1120) may be discarded and replaced with a new disposable cartridge after its air seal is broken to remove the AED distal electrode (115) or after use of the AED to defibrillate a patient (601).

The circuit-board cartridge (1125) and the disposable cartridge (1120) are preferably both sealed against air infiltration, although only the disposable cartridge (1120) must be configured to hold the AED pads in such a way as to prevent their exposure to the air. It is beneficial if the circuit-board cartridge (1125) is also sealed to prevent degradation of other electrical components of the AED held therein.

The compact AED (100) is configured to receive ECG signals (1205) (electrocardiogram signals) from a patient (601) while an AED proximate pad (405) and an AED distal pad (410) are within airtight storage. The compact AED (100) includes a device body (105), a circuit board (415); and two electrical connections on a surface (1115) of the device body (105) for purposes of measuring the ECG signals (1205) from the patient (601).

Whether in one or two cartridges, the device body (105) is configured for compact storage of the AED proximate pad (405) and the AED distal pad (410). The compact storage is configured to limit exposure of the AED proximate pad (405) and the AED distal pad (410) (referred to herein as "pads", or "AED pads") to air in order to prevent degradation of the AED pads that might otherwise occur in an oxygen environment.

The circuit board (415) is configured as an indivisible unit within the device body (105). It is indivisible because it may not be split into segments. More specifically, the circuit board (415) may not be divided into one functional unit in the device body (105) and another in the AED distal electrode (115). The circuit board (415) controls the defibrillation process and it is located within the device body (105), behind a front body housing (445).

The device body (105) has a first electrical connection between the circuit board (415) and a first defined location (1105) on the surface (1115) of the device body (105). The surface (1115) is used in order to enable placement of the electrodes on a patient (601) to take an ECG while the AED pads are in airtight storage. Thus, the first defined location (1105) and the surface (1115) are configured such that there is no increase in exposure of the AED proximate pad (405) or the AED distal pad (410) to air.

The device body (105) has a second electrical connection between the circuit board (415) and a second defined location (1110) on the surface (1115) of the device body (105). Preferably, the surface (1115) where the second electrode is located is the same surface used for the first electrical connection, but alternatively it may be a second surface. These first and second defined locations are preferably located nearby each other (e.g., within 3 to 5 inches on the same surface) so that when the surface (1115) with the electrical connections are placed on a patient (601), the two electrical connections can simultaneously read the patient's heart beat signals. A preferred embodiment places the first defined location and the second defined location on either hand of a person receiving an ECG. The second defined location (1110) and the surface (1115) are configured to not increase exposure of the AED proximate pad (405) and the AED distal pad (410) to air.

The electrical connection at each defined location may be flat, that is, flush with the surface (1115), or raised from the surface (1115). A raised or elevated, button-like projection of the electrical connection provides a potential to push the surface (1115) down on the patient (601) to enable better contact of the electrical connection with the patient (601).

The surface (1115) may be an interior panel when the device body (105) has two separable cartridges, one of these cartridges that holds the AED pads is configured to prevent exposure of the AED pads to air, which preferably means that it is airtight, but may also mean that it holds the AED pads in a sealed pouch. Preferably, as shown in FIG. 11, both AED pads are stored in the cartridge on the right in FIG. 11, which is the disposable cartridge (1120). Everything in FIG. 4 from the rear cover (465) through to the connecting electrode (130) is in the disposable cartridge (1120) in FIG. 11 on the right. The disposable cartridge (1120) has a backing with two pieces of conductive metal (not shown) that touch the first defined location (1105) and second defined location (1110), shown in FIG. 11.

Figure 13:
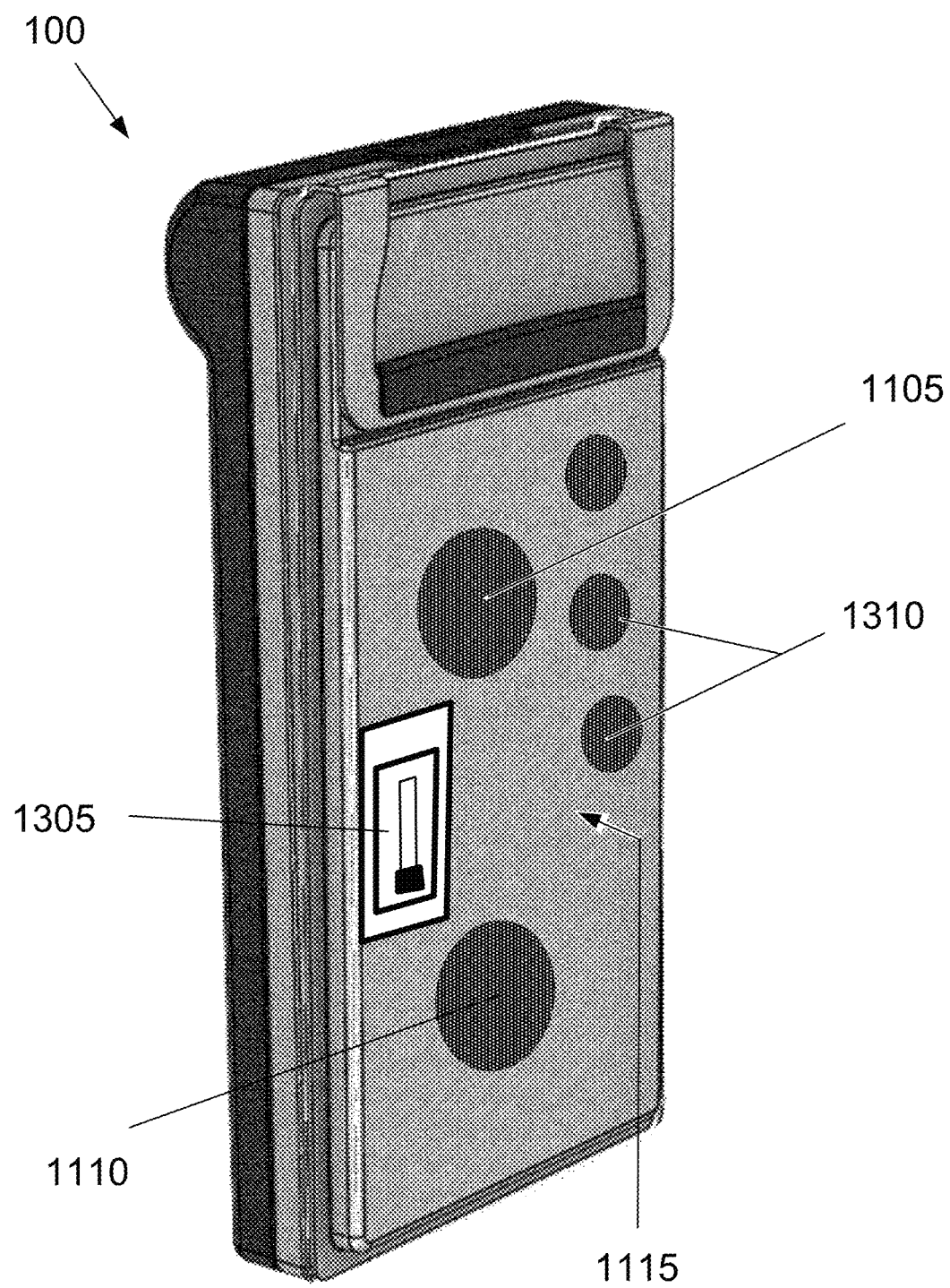
FIG. 13 is a perspective view of the device body holding all of the AED components in storage and showing the ECG electrodes on an external surface.

As shown in FIG. 11, these two separable cartridges can be mated together with a clip at the top and/or the bottom of one or both of the separable cartridges. Alternatively, the surface (1115) may be on an exterior surface of the device body (105), such as a rear cover (465) or the front of the front body housing (445). The rear-cover configuration is shown in FIG. 13. A potential embodiment would provide a 6-lead ECG using three electrodes where a person receiving the ECG touches two electrodes to either hand and a third to his or her ankle.

As shown in FIG. 11, the packing cover (455) may include a handle (1130) to remove the packing cover (455) and unseal the AED proximate pad (405) and AED distal pad (410).

In an alternative embodiment, the wire (120) is wrapped around a spool housed within the disposable cartridge (1120). The spool is configured to detach from the interior back cover housing when the AED distal pad (410) is deployed, allowing the wire (120) to easily uncoil. The circuit board (415) is further configured to receive ECG signals (1205) (to wit, heartbeat signals from the patient (601) when the first defined location (1105) and the second defined location (1110) on the surface (1115) of the device body (105) are put in contact with the patient (601).

In one potential embodiment, the AED proximate electrode (110) coincides with the first defined location (1105).

In another potential embodiment, the AED distal electrode (115) is attached to the AED distal pad (410) and the second defined location (1110) is electrically connected to the AED distal electrode (115).

The device body (105) may include an on-off switch (1305) between the second electrical connection and the circuit board (415). FIG. 13 shows a slider switch, but any switch may be used as long as the on-off switch (1305) is configured to prevent electrical flow between the AED distal electrode (115) and the circuit board (415) when the on-off switch (1305) is set to off. Preferably, the circuit board (415) is controlled by safety software and sensors that recognize when AED pads have been attached to the patient (601) or otherwise deployed to ensure that shocks cannot be inadvertently administered. The on-off switch (1305) is a backup mechanism to prevent accidental activation of the AED distal electrode (115) when the second defined location (1110) is electrically connected to the AED distal electrode (115), preferably through the connecting electrode (130).

The AED distal electrode (115) and an AED proximate electrode (110) are preferably configured to deliver an electrical charge when the AED proximate pad (405) and the AED distal pad (410) are attached to the patient (601). This electrical charge is preferably controlled by no other circuit board (415) positioned outside the device body (105).

The circuit board (415) is preferably configured to sense ECG signals (1205) from the patient (601) through a plurality of additional defined locations (1310) on the surface (1115) of the device body (105). These additional defined locations (1310) are preferably configured to not increase exposure of the AED proximate pad (405) and the AED distal pad (410) to air and said additional defined locations (1310) are further configured to sense the ECG signals (1205) when the additional defined locations (1310) are in electrical contact with the patient (601). Twelve-lead ECGs are taken using ten electrodes in very specific spots on the patient (601). This type of ECG is possible with the compact AED (100). When ten electrodes are used in a patient (601), the ten electrodes are preferably multiplexed into the first defined location (1105) and the second defined location (1110).

The number of additional defined locations (1310) on the surface (1115) may match the number of electrode sensors or may be less than the number of electrode sensors placed on the patient (601). Each defined location may be multiplexed, thereby reading multiple electrode sensors attached to that defined location.

Preferably, the circuit board (415) within the device body (105) holds a processor (470) configured to distinguish between multiple signals arriving at any single defined location, separating multiple ECG signals into separately identifiable ECG signals. Preferably, the processor (470) has capabilities of sending ECG signals and data to remote health care providers.

Alternatively, a computer (1210), wired or wirelessly connected to the circuit board (415), may be tasked with distinguishing between multiple signals arriving at any single defined location, separating multiple ECG signals into separately identifiable ECG signals. When present, the computer (1210) is preferably a mobile phone having capabilities of sending ECG signals and data to remote health care providers.

Multiplexing could also be accomplished by including a cartridge containing ECG electrodes. As an example, a 12-lead ECG that uses 10 electrodes would connect to fewer defined locations or electrical connections on the surface (1115). For example, 5 electrodes could go to the first defined location (1105) on the surface (1115) and 5 electrodes could go to the second defined location (1110). Multiplexing the signals from the patient (601) would determine which electrode is which. Alternatively, multiplexing could be accomplished by converting ECG analog signals to digital signals and then employing the computer to identify which electrode is which.

The circuit board (415) may be configured to receive ECG signals (1205) from more than two ECG sensors electrically connected to the patient (601). For example, this could happen when ECG sensors are wired up to the patient (601) and then attached to one of the defined locations on the device body (105). Wired connections are different from having a plurality of additional defined locations (1310) on the device body (105) because it embraces that more than two ECG sensors may be connected to a single defined location on the surface (1115) of the device body (105). Here again, the computer (1210) connected, preferably wirelessly, to the circuit board (415) is tasked with distinguishing between multiple signals arriving at the electrical connection at that single defined location on the surface (1115) of the device body (105). Preferably, the processor (170) has these capabilities and is within the device body (105).

Thus, there may be a plurality of ECG sensors configured to connect to the first defined location (1105), or to the second defined location (1110), or to the additional defined locations (1310).

The circuit board (415) may be connected, wired or wirelessly, to a speaker that is configured to audibly indicate the ECG signals (1205). Preferably, the speaker is within the device body (105), but alternatively may be within the computer (1210).

A screen may be configured to display the ECG signals (1205). The screen is preferably within the computer (1210).

The compact AED (100) is configured to deliver an electrical charge (605) to a patient (601) in cardiac distress. The compact AED (100) is further configured to support a plurality of cardiac rescues because it is reusable on another patient (601), preferably after the foam pad (460), AED distal electrode (115), and AED distal pad (410) are removed and replaced, and also after the AED proximate pad (405) and the liner (335) have been removed and replaced.

The compact AED (100) includes a device body (105) that houses the components of the compact AED (100), which may be referred to herein as the AED. The AED operationally functions using a circuit board (415) within the device body (105) that permits a battery (450) also within the device body (105) to energize both electrodes. The battery (450) is preferably lodged at the base of the device body (105) on its front side, which is shown in FIG. 4 on the right of the exploded view and within a front body housing (445). Preferably, the battery (450) is not part of, or mounted to, the circuit board. The rear cover (465) is shown to the left-side of the exploded view of the device body (105) in FIG. 4.

The device body (105) contains a AED proximate electrode (110) and a AED distal electrode (115). The AED proximate electrode (110) is an integrated part of the device body (105). It is preferably supplemented by a AED proximate pad (405), which is preferably made of an electrically conducting adhesive gel, such as hydrogel. If hydrogel is not used, the AED proximate pad (405) may include a skin adhesive (905) that is made to stick to the skin of a patient (601) in cardiac distress. An electrode adhesive (910) may be applied to adhere the AED proximate pad (405) to the AED proximate electrode (110). In another embodiment, the electrode adhesive (910) is attached to one or more conductive materials, which are then attached to the proximate electrode and the connecting electrode. In another embodiment, the electrode adhesive (910) is attached to one or more conductive materials, which are then attached to the first defined location (1105) and the second defined location (1110).

The AED proximate pad (405) is electrically conductive and is thus able to conduct the electrical charge (605) to or from the AED proximate electrode (110).

The AED proximate pad (405) is preferably the larger of the two pads. The AED proximate pad (405) is connected to the AED by adhering or fastening to the device body (105). The AED proximate pad (405) and the AED distal pad (410) are preferably made of hydrogel, but may also be conductive material such as carbon loaded vinyl or tin with any adhesive material. The term "pad" is used loosely in this sense that the AED proximate pad (405) and the AED distal pad (410) may be formed simply by applying hydrogel adhesive in lines, dashed lines, or lots of tiny dots. In practice, the substance forming the AED proximate pad (405) and the AED distal pad (410) may not be considered by some to be a pad in the traditional sense of it being a thick piece of soft material. Hydrogel or another adhesive may be similarly applied to the connecting electrode (130) and insulating cover (432). The connecting electrode (130) is preferably tin or silver. In an alternative embodiment, a wire (120) is attached to a distal conductive material which is then connected to the connecting electrode (130).

Thus, the device body (105) is configured to operably integrate with the AED proximate electrode (110). To facilitate reuse of the AED with new adhesive pads, the AED proximate pad (405) is a removable part of the AED proximate electrode (110) and also a removable part of the device body (105). The AED proximate electrode (110) is restored to near-new condition by peeling off the used AED proximate pad (405) and adhering a new replacement pad to the AED proximate electrode (110). The AED proximate pad (405), liner (335), AED distal pad (410), AED distal electrode (115), foam pad (460), and packing cover (455) may also be removed and replaced should that become necessary for any reason.

In an alternative embodiment shown in FIG. 11, the AED proximate pad (405), the AED proximate electrode (110), liner (335), AED distal pad (410), AED distal electrode (115), foam pad (460), and packing cover (455) are a separately sealed and replaceable part of the device body (105), which is referred to as the disposable cartridge (1120). The disposable cartridge (1120) is part of the device body (105). The disposable cartridge (1120) is attachable to the front body housing (445) and includes a packing cover (455), which is removable, to seal the AED proximate pad (405) the AED proximate electrode (110), liner (335), AED distal pad (410), AED distal electrode (115), and foam pad (460). In this embodiment, the disposable cartridge (1120) includes conductive material to connect with the AED proximate electrode (110) and the connecting electrode (130).

The AED distal electrode (115) is configured to be easily unpacked from the device body (105) to deploy on the patient (601) in cardiac distress. Preferably, a liner (335) is placed between the two electrodes so that the AED distal electrode (115) can be easily separated from the AED proximate electrode (110) and unpacked from the device body (105). More precisely, in a preferred embodiment, the liner (335) is placed between the AED proximate pad (405) and the AED distal pad (410) to keep them from sticking together when separated during an emergency. The liner (335), the AED proximate pad (405), AED distal electrode (115), AED distal pad (410), foam pad (460), packing cover (455), wire (120), and insulating cover (432) are user replaceable.

In another embodiment, a second liner is provided on the other side of the AED proximate pad (405) prior to installation onto the AED proximate electrode (110) to aid in shipping and packaging the AED proximate pad (405), or to maintain the adhesive prior to assembly against the back cover (FIG. 11). This second liner faces the AED proximate electrode (110) and is removed from the AED proximate pad (405) prior to installation on the AED proximate electrode (110) or the disposable cartridge (1120) at the front body housing (445).

In an alternative embodiment, the AED distal electrode (115), the AED proximate electrode (110), the connecting electrode (130), the AED proximate pad (405) or the AED distal pad (410) can made of a carbon-loaded vinyl, which is an electrically conductive material and can serve as a substitute for tin or silver.

In another alternative embodiment, the AED distal electrode (115) is twice the size of the pad geometry and then folded over on itself with the splayed wire strands between the layers of AED distal electrode (115). A layer of electrode adhesive (910) holds together the strands (125) of the wire (120) and the folded AED distal electrode (115). The benefit of this embodiment is that it provides a higher level of surface area between the AED distal electrode (115) and the strands (125).

Figure 2:
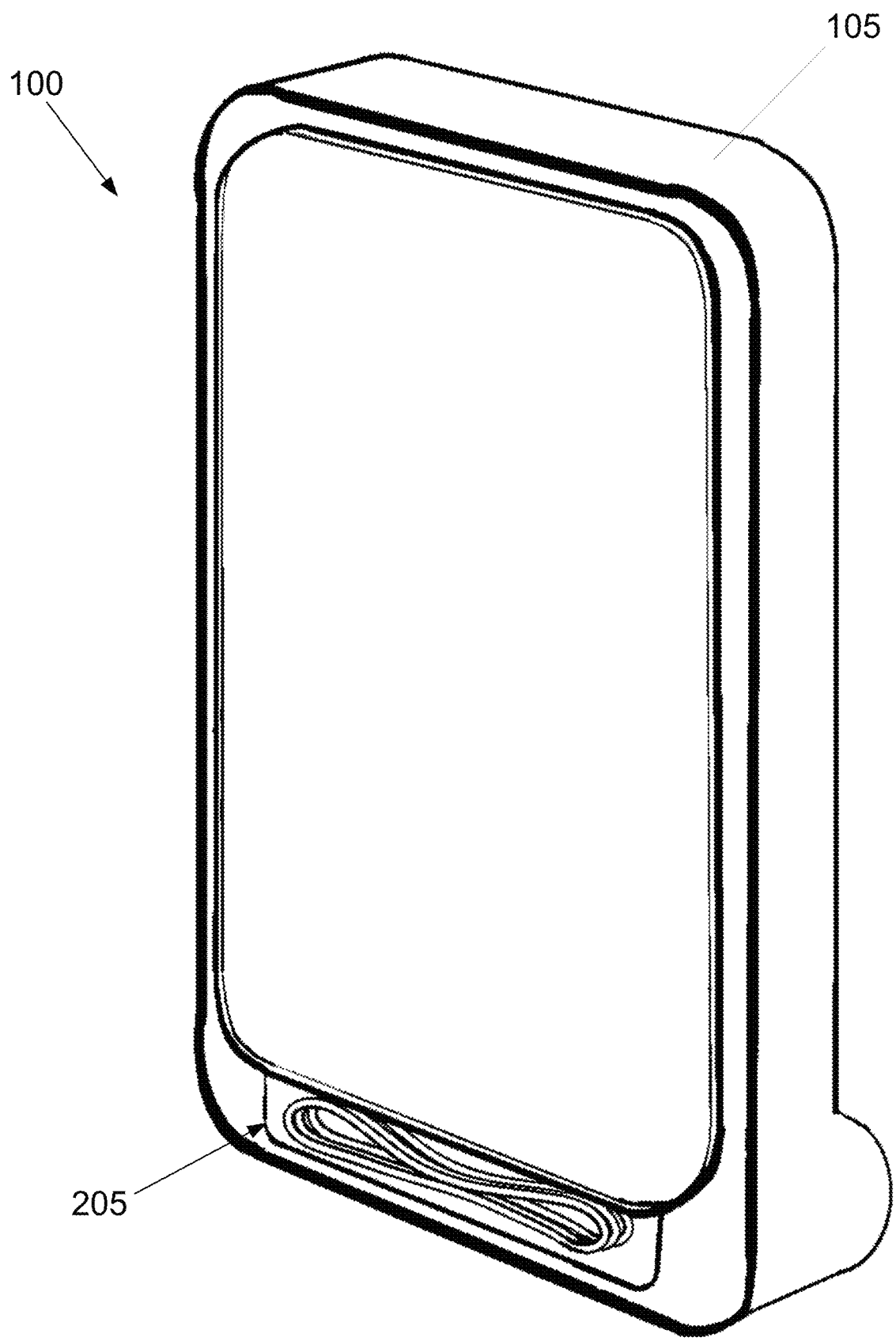
FIG. 2 is a perspective view of the compact AED with one distal electrode without a rear cover.

The AED distal electrode (115) does not require a typical electrical connector like other AEDs (such as a plug), makes contact to the connecting electrode (130) on the device body (105), and only requires a single wire or cord. The wire (120) preferably stores in a carve-out (205) toward the rear of the device body immediately to the front of where the rear cover (465) would go when added to device body shown in FIG. 2.

Most commonly, the gel used for AED electrodes is typically an adhesive gel, such as hydrogel. Typically, no other adhesive coating is needed with this type of gel. Optionally, the AED proximate pad (405) may be coated with one or more adhesives on each side of the AED proximate pad (405) for attachment to the AED proximate electrode (110) and for attachment to the patient (601) once the AED distal electrode (115) is unpacked. While the adhesive may be used at different locations within the AED and may be the same adhesive in composition, each adhesive at a different location is given a distinct name to accommodate the potential for different adhesives being used and to avoid confusion. The adhesive that sticks to a patient's skin is referred to as a skin adhesive (905). The adhesive used to stick the AED proximate pad (405) to the AED proximate electrode (110), to stick the AED proximate pad (405) to the conductive material of the disposable cartridge (1120), to stick the insulating cover (432) and the wire (120) to the conductive material of the disposable cartridge (1120), to stick the AED distal pad (410) to the AED distal electrode (115), and to stick the insulating cover (432) and wire (120) to the connecting electrode (130) is referred to as the electrode adhesive (910). Finally and preferably, the adhesive may be used to seal the device body (105) from air infiltration. The preferred adhesive (320) is preferably a silicone adhesive. Other methods to preclude air infiltration may include plastic pouches for the AED pads, sonic welding or other mechanical sealing techniques.

The AED distal electrode (115) is electrically connected from the device body (105) by a wire (120). The wire (120) must be of sufficient gauge and otherwise configured to deliver the electrical charge (605) to the AED distal electrode (115) from the device body (105). The AED distal electrode (115) is configured to be replaceable and further configured to be operable by the circuit board (415) in the device body (105). No other circuit board positioned outside the device body, for example, one in or on the distal electrode is needed. Preferably, the AED distal electrode (115) is configured to be exclusively operable by the circuit board (415) in the device body (105).

Preferably, the circuit board (415) in device body (105) of the compact AED (100) is configured to deliver a reversal of the electrical polarity of the electrical charge (605) during the time the AED is delivering a charge to the patient (601). This is termed a biphasic charge or shock. With any biphasic shock, the direction of current flow is reversed during the electrical defibrillation cycle. In the preferred embodiment of the compact AED (100), such reversal is implemented at least one time while delivering the electrical charge (605).

Preferably, the circuit board (415) is configured to be an indivisible unit within the device body (105). This means that the circuit board (415) is not separable into two or more circuit board components. While there may be more than one printed circuit board (PCB) within the device body (105), none such PCB may be broken off from another PCB and preferably, none is located in the AED distal electrode (115).

The compact AED (100) preferably employs the AED proximate pad (405) on the device body (105) so that the AED proximate pad (405) may be peeled off the device body (105). While an electrical plug provides a relatively easy means for disconnecting any electrical component, the preferred connection for the AED proximate electrode (110) to the circuitry within the device body (105) is one involving electrical contact with the circuit board. A clip, a fastener, hydrogel and/or an adhesive may be employed to secure this contact. In an alternative embodiment, the AED proximate pad (405) the AED proximate electrode (110), the liner (335), the AED distal pad (410), the AED distal electrode (115), the foam pad (460), and the packing cover (455) are a separately sealed and replaceable part of the device body (105), referred to as the disposable cartridge (1120). The disposable cartridge (1120) fastens to the front body housing (445).

The compact AED (100) is preferably configured with the wire (120) composed of strands (125) of smaller diameter wires. The strands (125) are attached to the device body (105) after splaying the strands (125) on a terminal or connecting electrode (130) on the device body (105). The strands (125) may be embedded in a hardened, electrically conducting gel (431), preferably hydrogel, to make adhesion to the connecting electrode (130) easier for replacement. This arrangement is shown in FIG. 4 where the splayed wires are embedded in a hardened, electrically conducting gel (431), such as hydrogel, which can then be adhered to the connecting electrode (130). For that arrangement, there is preferably an insulating cover (432) over the gel and wires to insulate them. Because the AED distal electrode (115) and the AED proximate electrode (110) have separated electrical connections a biphasic shock is made possible. The wire (120) that connects the AED distal electrode (115) to the device body (105) is preferably splayed to flatten or minimize the height or profile of the connections. In an alternative embodiment, the wire is mechanically connected to a conductive terminal on the disposable cartridge (1120) and the insulating cover (432) is constructed of epoxy.

In another alternative embodiment, the strands (125) that are embedded in a hardened, electrically conducting gel (431) are adhered to carbon-loaded vinyl, tin, or silver with electrode adhesive (910) which may be the same material as the hardened, electrically conducting gel (431). The carbon-loaded vinyl, tin or silver is covered with the insulating cover (432).

In another alternative embodiment, the strands (125) that are embedded in a hardened, electrically conducting gel (431) are folded between a carbon-loaded vinyl, tin, or silver, which are electrically conductive materials. The hardened, electrically conducting gel (431) and the strands (125) are adhered to the carbon-loaded vinyl, tin, or silver with the electrode adhesive (910), which may be the same material as the hardened, electrically conducting gel (431). The carbon-loaded vinyl, tin or silver is covered with the insulating cover (432).

Similarly, the wire connection at the other end of the wire (120) on the AED distal electrode (115) may use splayed strands. The wire (120) is preferably attached to the AED distal electrode (115) after splaying its strands (125) on the AED distal electrode (115).

The AED distal electrode (115) preferably comprises a metal conductor (preferably tin or silver) with a AED distal pad (410) on one side next to the liner (335) adhered to the metal conductor and a foam pad (460) covering the other side of the metal conductor next to a packing cover (455). Preferably, the foam pad (460) AED distal electrode (115), and AED distal pad (410) is a unit. Once used, this unit is disconnected and discarded, along with the wire and a new unit is installed with a new wire. In another embodiment, the AED distal pad (410) is configured to be peeled off and removed from the AED distal electrode (115) when a replacement distal pad is needed. In addition, the AED distal electrode (115) is configured to be disconnected from the connecting electrode (130) at the device body (105). For example, this may be accomplished by peeling off the wire (120) and hydrogel from the connecting electrode (130), by removing the wire (120) from the connecting electrode (130), by unplugging from the device body (105), or by any other means. In an alternative embodiment, the proximal electrode can also be disconnected from the device body when an electrical plug is not present, such as when it may need to be replaced for maintenance, in the event it is combined with the AED proximate pad (405), or any other reason. In yet another embodiment, the connecting electrode can also be disconnected from the device body when an electrical plug is not present, such as when it may need to be replaced for maintenance, in the event it is combined with the insulating cover (432), or any other reason.

The device body (105) is configured to store the AED proximate electrode (110) separated from the AED distal electrode (115) by a liner (335). The liner (335) is preferably a thin plastic sheet that can be easily pulled off both electrodes to free them from their storage position. Thus, the device body (105) is preferably configured to store the proximate electrode and the AED distal electrode (115) within the device body (105) separated by the liner (335).

The liner (335) is preferably configured to define a hole (425) through which an electrical connection is made between the AED pads on the AED proximate electrode (110) and the AED distal electrode (115) enabling activation of a check on the operability of a discharge circuit. This electrical connection facilitates periodic testing of the AED pads, for example the hydrogel, by the compact AED (100) when activated to do a simple connectivity test. Doing this would validate that the user has correctly stored the AED pads and that the electrical path is valid (i.e., the hydrogel has not dried out).

The discharge circuit is an electrical path from the device body (105) that houses the AED proximate electrode (110), through the hole (425) to the AED distal electrode (115), and back through the wire (120). In an alternative embodiment, the discharge circuit is an electrical path from the device body (105) through the wire (120) to the AED distal electrode (115), through the hole (425), to the AED proximate electrode (110).

When in use, the circuit board (415) is configured to deliver the electrical charge (605) through the connecting electrode (130), through the wire (120) through the AED distal electrode (115) where the electrical charge (605) passes through the patient (601) and ends at the AED proximate electrode (110). When a biphasic charge is employed, the circuit board (415) is also configured to deliver the electrical charge (605) through the AED proximate electrode (110), through the patient (601), through the AED distal electrode (115), through the wire (120), and end at the connecting electrode (130). In other embodiments of a biphasic shock, the first electrical path may begin with the proximate electrode and then switch to the distal electrode.

Figure 7:
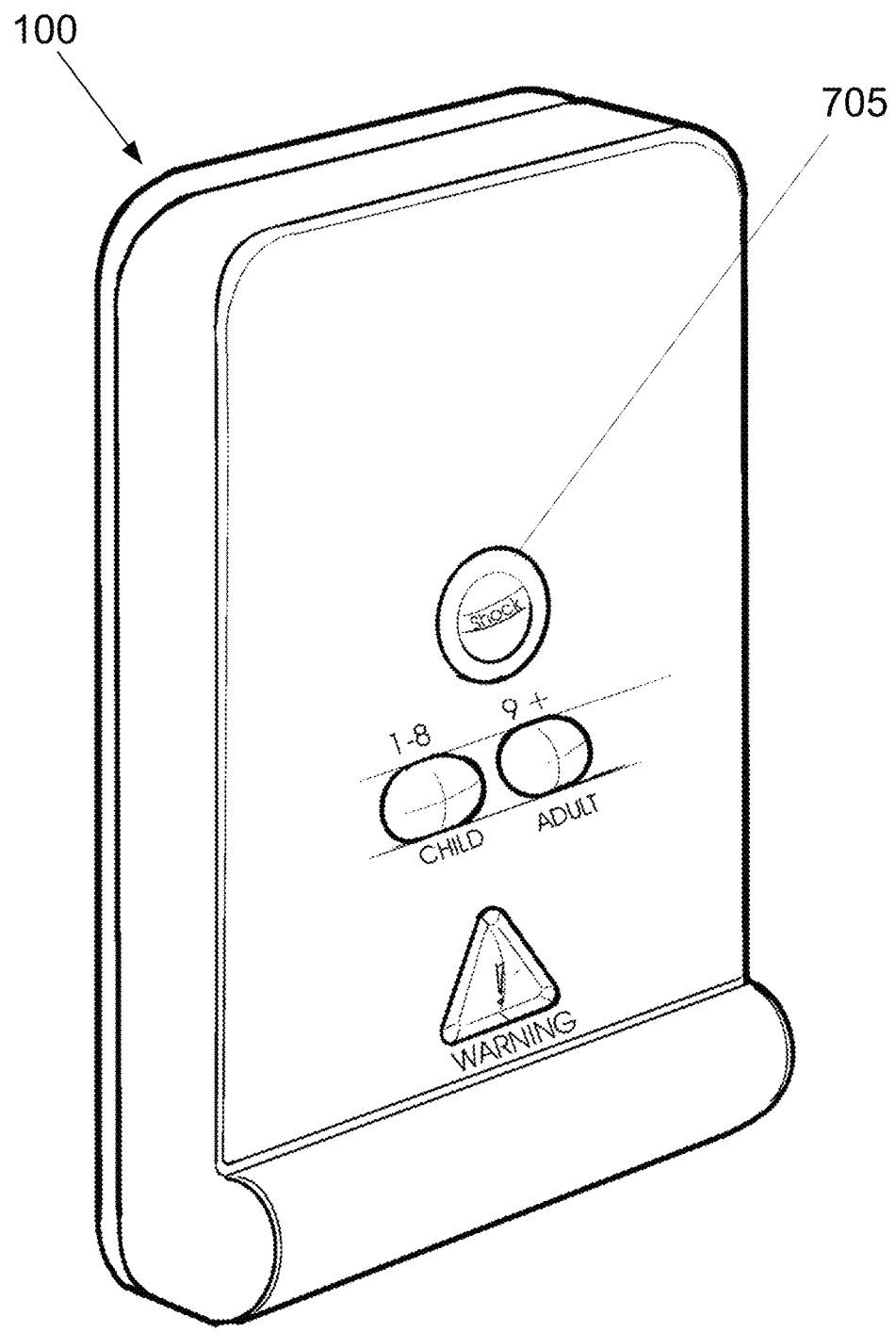
FIG. 7 is a perspective view of the front of the compact AED with one distal electrode.

As an example, FIG. 7 shows an activation button (705) along with other controls on the front face of the compact AED (100). In this embodiment, the activation button (705) enables use of the AED to send the electrical charge (605) through the patient (601). Other embodiments include automatic activation of the AED, for example when an arrhythmia is detected.

Figure 3:
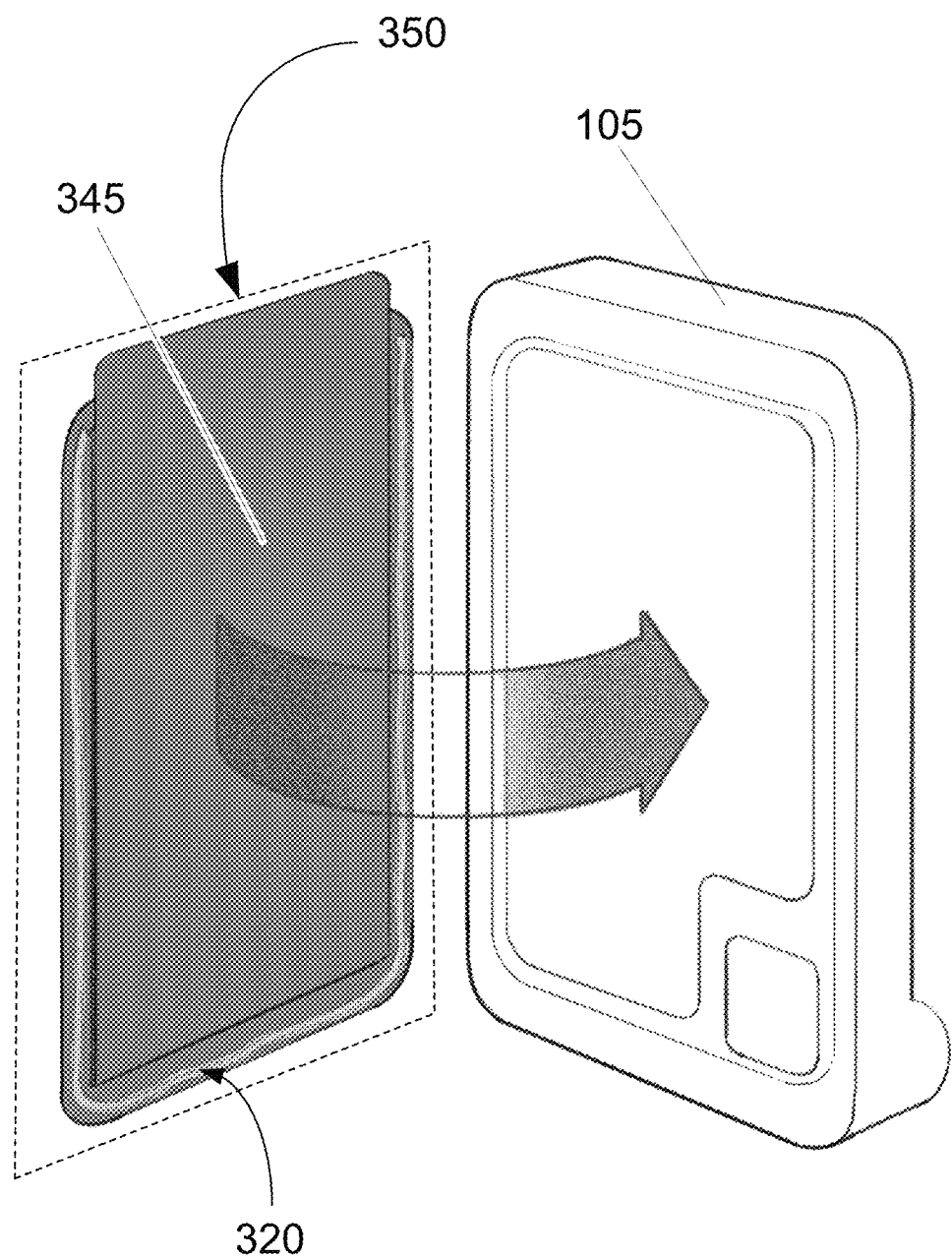
FIG. 3 is a perspective view of the device body and packaging envelope.

A packaging envelope (350) is shown in FIG. 3 within the rectangular dashed box. A pull-tab (345) may be used to unseal the packaging envelope (350). The packaging envelope (350) is configured to seal the AED proximate pad (405) and AED distal pad (410) to help keep them or prevent them from drying out when in storage, and the pull-tab (345) is configured to easily open the packaging envelope (350) during a rescue in order to reveal the AED proximate pad (405) and align it to the proximal electrode.

A metalized surface (420) on the device body (105) may be applied to help seal the device body (105) from air entering and leaving the device body (105). Among other benefits, the metalized surface (420) prevents the AED pads from drying out. Thus, the metalized surface (420) is configured to seal the device body (105) when the components of the AED are in storage.

Figure 8:
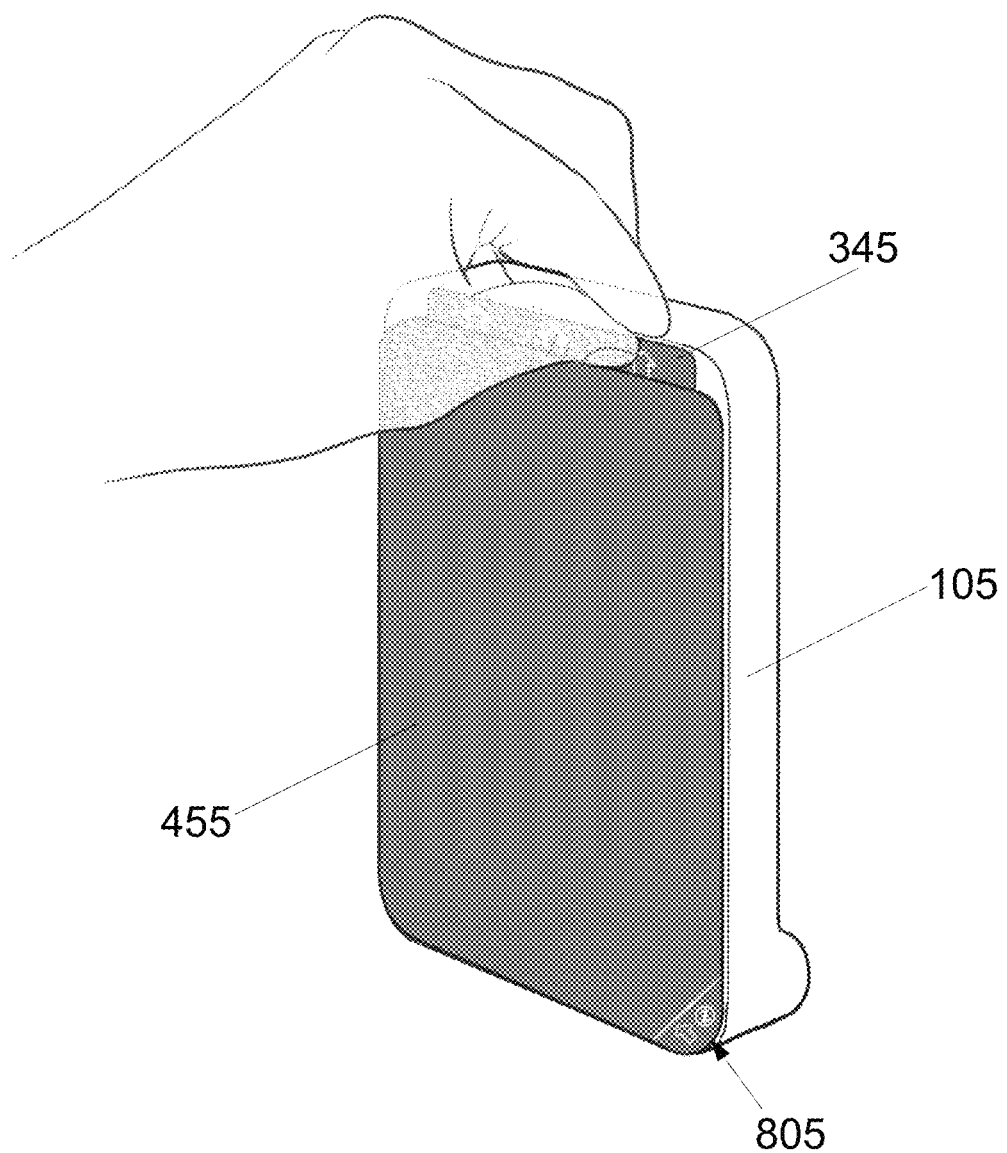
FIG. 8 is rear view of the device body with a packing cover over a packaging envelope with a pull-tab.
Figure 9:
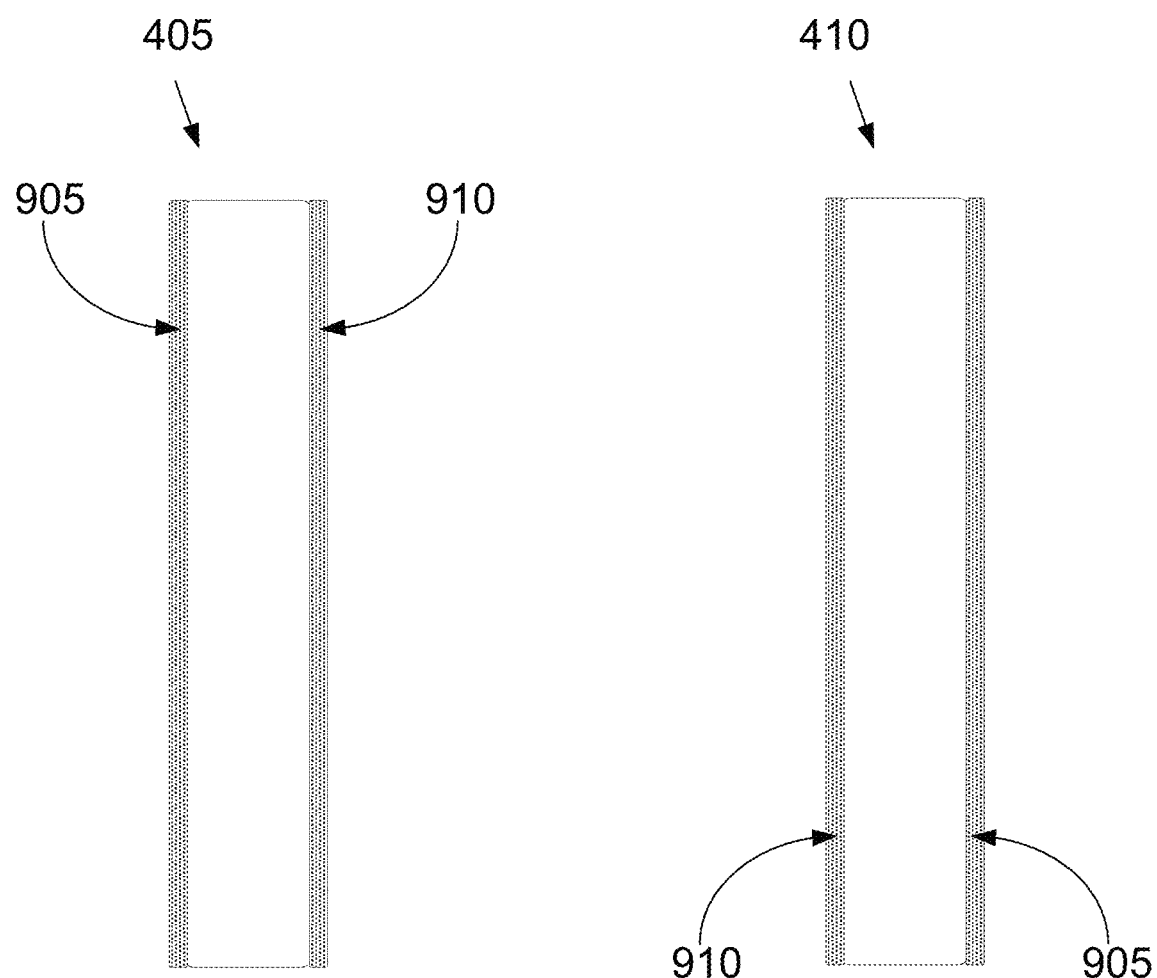
FIG. 9 is a side view of the proximate pad and the distal pad showing the skin adhesive and the electrode adhesive.
Figure 10:
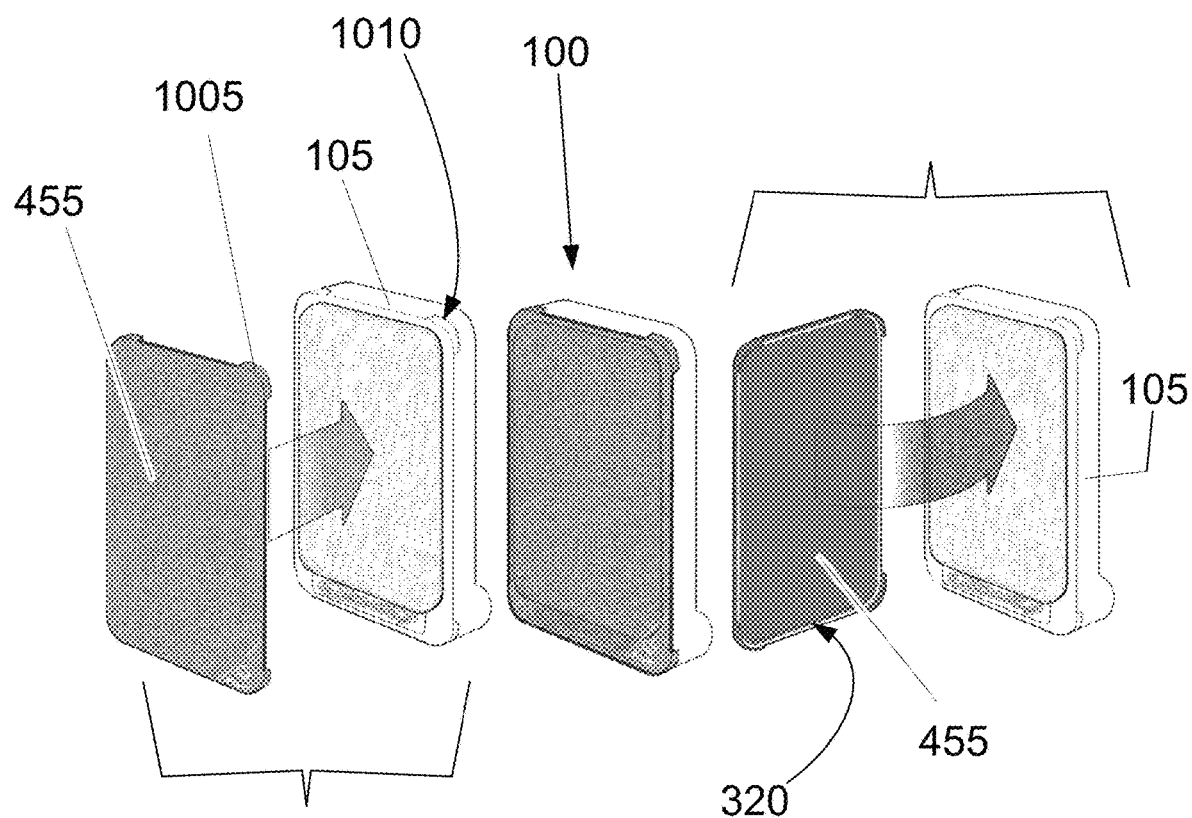
FIG. 10 is a perspective view of an alternative embodiment where the rear cover and packing cover are combined, to comprise a plastic that has an adhesive around the periphery to seal to the device body.

As shown in FIG. 4, a rear cover (465) is a rigid closure for the device body (105). The rear cover (465), for example, could be a hard plastic. An adhesive (320), such as silicone, may be used on the periphery of the packaging envelope (350) to engage with the device body (105). Additionally, a packing cover (455) may be included to help seal up the device body (105) when the components are stored therein. The packing cover (455), like the rear cover (465), is preferably made of a light weight material, such as plastic, foam, or that is metalized material. For example, a metalized coating or seal would be peeled away at the corner or edge of the device. A peelable corner tab (805) is shown in FIG. 8 for the lower right-hand corner of the packing cover (455). The disposable cartridge (1120) may comprise a conductive material to allow an electrical connection between the AED proximal electrode (110) and the AED proximal pad (405) and between the AED distal electrode (115) and the connecting electrode (130).

In an alternative embodiment, the packing cover (455) may serve to replace the foam pad (460), revealing the AED distal electrode (115) and AED distal pad (410) underneath of it once removed.

The rear cover (465) may be combined with the packing cover (455). The packing cover (455) is preferably composed of plastic and is sealed to the device body (105) with adhesive (320) around the periphery of the packing cover (455). The adhesive (320) is preferably silicone adhesive. In another embodiment, the packing cover (455) may be configured with a corner clip (1005), preferably 4 corner clips at each corner of the packing cover (455). Such clips may also be present on the rear cover (465) and the rear cover (465) itself may also be sealed to the device body with adhesive (320). Preferably, each corner clip (1005) mates with a notch (1010) on the device body (105), which ensures a tight fit, and a seal by the adhesive (320). The plastic of the packing cover (455) may seal against a metalized surface (420) on the device body (105) to help prevent air infiltration. When cartridges are used, use of the metalized surface (420) will help prevent air infiltration to the circuit-board cartridge (1125) and/or the disposable cartridge (1120).

In another embodiment, the rear cover (465) may be configured with a mechanism, such as a notch or clip, to mate with a mechanism on the device body (105), such as a notch or clip, to ensure proper orientation of the connecting electrode (130).

In another alternative embodiment, the packing cover (455) may serve to replace the rear cover (465), revealing the distal assembly, namely the foam pad (460), AED distal electrode (115) and AED distal pad (410), underneath of it once removed. Adhesive sealant around the inside of the packing cover (455) connects to the device body (105) and prevents air infiltration to the AED pads.

In sum, important component parts of the compact AED (100) include: the foam pad (460), the AED distal electrode (115), and the AED distal pad (410), which are an assembly, and which adhere to the patient in cardiac distress; the electrodes, including the AED distal electrode (115) and the AED proximate electrode (110), which are conductive metals, preferably tin or silver, which form the conductive portion that connect to the patient in cardiac distress and also the AED distal electrode (115) is the component that connects to the wire (120) that then connects to the device body (105); the AED distal pad (410) and the AED proximate pad (405), which are preferably made of hydrogel and which include an electrically conductive gel that adheres each electrode to the patient and that creates a lower resistance electrical path to the patient; the AED proximate electrode (110) and the AED distal electrode (115), which are electrically conductive elements that are connected to AED's internal circuitry.

The above-described embodiments including the drawings are examples of the compact AED (100) and merely provide illustrations of the compact AED (100). Other embodiments will be obvious to those skilled in the art. Thus, the scope of the compact AED (100) is determined by the appended claims and their legal equivalents rather than by the examples given.

INDUSTRIAL APPLICABILITY

The compact AED (100) has application to the medical industry.

What is claimed is:

1. A compact automated external defibrillator (AED) configured to receive ECG signals (electrocardiogram signals) from a patient while an AED proximate pad and an AED distal pad are within airtight storage, the compact automated external defibrillator comprising:
    a device body configured for a compact storage of the AED proximate pad and the AED distal pad, the compact storage configured to limit exposure of the AED proximate pad and the AED distal pad to air;
    a circuit board configured as an indivisible unit within the device body;
    the device body comprising a first electrical connection between the circuit board and a first defined location on a surface of the device body, said surface configured to not increase exposure of the AED proximate pad and the AED distal pad to air;
    the device body further comprising a second electrical connection between the circuit board and a second defined location on the surface of the device body; and
    the circuit board further configured to receive the ECG signals from the patient when the first defined location and the second defined location on the surface of the device body are put in contact with the patient.

2. The compact automated external defibrillator of claim 1, wherein a proximate electrode coincides with the first defined location.

3. The compact automated external defibrillator of claim 1 further comprising an AED distal electrode attached to the AED distal pad, wherein the second defined location is electrically connected to the AED distal electrode.

4. The compact automated external defibrillator of claim 3, wherein the device body further comprises an on-off switch between the second electrical connection and the circuit board, the on-off switch configured to prevent electrical flow between the AED distal electrode and the circuit board when the on-off switch is set to off.

5. The compact automated external defibrillator of claim 1, wherein an AED distal electrode and an AED proximate electrode are configured to deliver an electrical charge when the AED proximate pad and the AED distal pad are attached to the patient, said electrical charge controlled by no other circuit board positioned outside the device body.

6. The compact automated external defibrillator of claim 1, wherein the circuit board is configured to sense ECG signals from the patient through a plurality of additional defined locations on the surface of the device body, said additional defined locations configured to not increase exposure of the AED proximate pad and the AED distal pad to air and said additional defined locations further configured to sense the ECG signals when the additional defined locations are in electrical contact with the patient.

7. The compact automated external defibrillator of claim 1, wherein the circuit board is configured to receive ECG signals from more than two ECG sensors electrically connected to the patient.

8. The compact automated external defibrillator of claim 1, further comprising a plurality of ECG sensors configured to connect to the first defined location.

9. The compact automated external defibrillator of claim 1, further comprising a plurality of ECG sensors configured to connect to the second defined location.

10. The compact automated external defibrillator of claim 1, further comprising a speaker configured to audibly indicate the ECG signals.

11. The compact automated external defibrillator of claim 1, further comprising a screen configured to display the ECG signals.

12. The compact automated external defibrillator of claim 1, wherein the device body is connected wirelessly to a computer for display of the ECG signals.

13. The compact automated external defibrillator of claim 1, wherein the device body is connected wirelessly to a computer to audibly transmit the ECG signals.

* * * * *